US009259460B2

(12) United States Patent
Contorni (10) Patent No.: US 9,259,460 B2
(45) Date of Patent: *Feb. 16, 2016

(54) COMBINATION VACCINES WITH LOW DOSE OF HIB CONJUGATE

(75) Inventor: Mario Contorni, Siena (IT)

(73) Assignee: GLAXOSMITHKLINE BIOLOGICALS SA, Siena (IT)

(*) Notice: Subject to any disclaimer, the term of this patent is extended or adjusted under 35 U.S.C. 154(b) by 723 days.

This patent is subject to a terminal disclaimer.

(21) Appl. No.: 13/250,094

(22) Filed: Sep. 30, 2011

(65) Prior Publication Data

US 2012/0107346 A1   May 3, 2012

Related U.S. Application Data

(63) Continuation of application No. 10/593,007, filed as application No. PCT/IB2005/000927 on Mar. 14, 2005, now abandoned.

(30) Foreign Application Priority Data

Mar. 15, 2004 (GB) .................................. 0405787.3

(51) Int. Cl.
| | | |
|---|---|---|
| A61K 39/095 | (2006.01) | |
| A61K 39/08 | (2006.01) | |
| A61K 39/05 | (2006.01) | |
| A61K 39/02 | (2006.01) | |
| A61K 39/102 | (2006.01) | |

(52) U.S. Cl.
CPC ................ *A61K 39/08* (2013.01); *A61K 39/05* (2013.01); *A61K 39/099* (2013.01); *A61K 39/102* (2013.01)

(58) Field of Classification Search
None
See application file for complete search history.

(56) References Cited

U.S. PATENT DOCUMENTS

| 6,333,036 B1 | 12/2001 | Arminjon et al. |
| 6,756,040 B2 | 6/2004 | Peetermans et al. |
| 2003/0180316 A1 | 9/2003 | Boutriau et al. |

FOREIGN PATENT DOCUMENTS

| WO | WO 97/00697 A | 1/1997 |
| WO | WO 02/00249 A2 | 1/2002 |

OTHER PUBLICATIONS

Communication of Notice of Opposition Against the Grant of EP 1725258B1, European Patent Office, 14 pages total, Jun. 24, 2011.
Reply to Notice of Opposition Against EP 1725258B1, European Patent Office, 9 pages total, Jan. 25, 2012.
Notice of Opposition to EP-B-0 833 662, European Patent Office, 23 pages total, Dec. 21, 2001.
Asensi et al., "Immunogenicity and Safety in Infants of a DTwPHib Full Liquid Vaccines", Acta Paediatr, 92:541-545 (2003).
Kanra et al., "Effect of Aluminum Adjuvants on Safety and Immunogenicity of Haemophilus Influenzae Type b-CRM 197 Conjugate Vaccine", Pediatrics International, 45:314-318 (2003).
Tamm et al,. "Double-Blind Study Comparing the Immunogenicity of a Licensed DTwPHib-CRM197 Conjugate Vaccine (Quattvaxem) With Three Investigational, Liquid Formulations Using Lower Doses of Hib-CRM197 Conjugate", Vaccines, 23:1715-1719 (2005).
Amir, et al., "Immunogenicity and Safety of a Liquid Combination of DT-PRP-T Vs. Lyophilized PRP-T Reconstituted With DTP," Vaccine 15(2):149-154 (1997).
Black, et al., "Safety of Combined Oligosaccharide Conjugate Haemophilus Influenzae Type b (HbOC) and Whole Cell Diptheria-Tetanus Toxoids-Pertussis Vaccine in Infancy," *Ped Inf Dis J* 12(12):981-985 (1993).
Campbell, et al., "Standard and Alternative Regimens of Haemophilus Influenzae Type b Conjugate Vaccine (Polyribosylribitol Phosphate-Tetanus Toxoid Conjugate Vaccine) Elicit Comparable Antibody Avidities in Infants," *Pediatr Infect Dis J* 21:822-826 (2002).
Eskola, et al., "Randomised Trial of the Effect of Co-Administration With Acellular Pertussis DTP Vaccine on Immunogenicity of Haemophilus Influenzae Type b Conjugate Vaccine," *Lancet* 348:1688-1692 (1996).
Fernandez, et al., "Randomized Trial of the Immunogenicity of Fractional Dose Regimens of PRP-T Haemophilus Influenzae Type B Conjugate Vaccine," *Am J Trop Med Hyg* 62(4):485-490 (2000).
Guimaraes, et al., "Antibody Response to Haemophilus Influenzae Type b Tetanus Conjugate Vaccine With Two Doses Given At 3 and 5 Months of Age," *Int J Infect Dis* 6:113-117 (2002).
Kanra, et al., "Effect of Aluminum Adjuvants on Safety and Immunogenicity of Haemophilus Influenzae Type b-$CRM_{197}$ Conjugates Vaccine," *Ped Int* 45(3):314-318 (2003).
Lagos, et al., "Economisation of Vaccination Against Haemophilus Influenzae Type b: A Randomized Trial of Immunogenicity of Fractional-Dose and Two-Dose Regimens," *Lancet* 351(9114):1472-1476 (1998).
Nicol, et al., "Haemophilus Influenzae Type b Conjugate Vaccine Diluted Tenfold in Diptheria-Tetanus-Whole Cell Pertussis Vaccine: A Randomized Trial," *Pediatr Inf Dis J* 21(2):138-141 (2002).
Nolan, et al., "A Combination of Liquid Hib (PRP-OMPC), Hepatitis B, Diptheria, Tetanus and Whole-Cell Pertussis Vaccine: Controlled Studies of Immunogenicity and Reactogenicity," *Vaccine* 19(15-16):2127-2137 (2001).
Pines, et al., "New Acellular Pertussis-Containing Paediatric Combined Vaccines," *Vaccine* 17(13-14):1650-1656 (1999).

(Continued)

*Primary Examiner* — Jennifer Graser
(74) *Attorney, Agent, or Firm* — Roberta L. Robins (57) ABSTRACT

Provided herein are combination vaccines comprising antigens for protecting a subject against at least diphtheria, tetanus, pertussis and Hib, wherein: (a) the antigen for protecting against Hib is a conjugate of a Hib capsular saccharide; (b) the concentration of the Hib conjugate in the vaccine is <15 μg/ml; and (c) the Hib conjugate has never been lyophilized.

23 Claims, 1 Drawing Sheet

(56) References Cited

OTHER PUBLICATIONS

Robinson, "DTP-HBOC Diptheria and Tetanous Toxoids and Pertussis Vaccine Adsorbed and Haemophilus B Conjugate Vaccine," *Drugs of Today / Medicamentos De Actualidad* 29(7):463-464 (1993) XP008052438.

Sturgess, et al., "Haemophilus Influenzae Type b Conjugate Vaccine Stability: Catalytic Depolymerization of PRP in the Presence of Aluminum Hydroxide," *Vaccine* 17:1169-1178 (1999).

Tamm, et al., "Double-Blind Study Comparing the Immunogenicity of a Licensed DTwPHib-CRM197 Conjugate Vaccine (Quattvaxem(TM)) With Three Investigational, Liquid Formulations Using Lower Doses of Hib-CRM197 Conjugate," *Vaccine* 23(14):1715-1719 (2005).

CDC published documentation of line, printed on 2010, Apr. 12, 2010.

Tauxe R Emerfing Infectious Disease, 2001, vol. 7, No. 3, pp. 516-521.

Asensi et al. Acta Paediatri May 2003, vol. 92, pp. 541-545.

Gupta et al., Biologicals, Jun. 1999, vol. 27, No. 2, pp. 167-176.

Kanra et al., Pediatrics International Jun. 2003, vol. 45, No. 3, pp. 314-318.

COMBINATION VACCINES WITH LOW DOSE OF HIB CONJUGATE

CROSS-REFERENCE TO RELATED APPLICATIONS

This application is a continuation application of U.S. patent application Ser. No. 10/593,007, filed Dec. 2, 2008 now abandoned which is a 35 U.S.C. §371 filing of PCT/IB2005/000927, Filed Mar. 14, 2005 which claims the benefit of Great Britain Application No. 0405787.3, filed Mar. 15, 2004, from which applications priority is claimed pursuant to 35 U.S.C. §§119 and 120 and which applications are hereby incorporated by reference in their entireties.

TECHNICAL FIELD

This invention is in the field of combination vaccines, particularly those for protecting against diphtheria, tetanus, pertussis and *H. influenzae* type b ('Hib').

BACKGROUND ART

Combination vaccines including antigens for immunising against diphtheria, tetanus, pertussis and Hib are known ('DTP-Hib' vaccines). Three such vaccines have been marketed under the names TETRAMUNE™ and QUATVAXEM™ (which use cellular pertussis antigens 'DTwP-Hib') and INFANRIX-Hib™ (which uses acellular pertussis antigens 'DTaP-Hib').

The inclusion of Hib-conjugate components in DTaP-Hib vaccines has been associated with reductions in the anti-Hib response [1, 2]. Furthermore, Hib-conjugates are unstable in aqueous media and cannot survive prolonged storage in this form [3]. For this reason, in combination vaccines that include Hib-conjugate antigens, it is common for the Hib component to be provided as a lyophilised powder that is reconstituted at the time of delivery with a liquid formulation of the other antigens.

Hib-conjugate antigens are not cheap to produce, and there is concern that their cost will inhibit widespread use in developing countries, and so alternative strategies for Hib-conjugate use have been developed [4-6]. One approach to furthering their use has been to give two doses (e.g. at 3 & 5 months of age [5] or at 4 & 6 months [6]), rather than the normal three doses (2, 4 & 6 months [7]). In a different approach, whereas Hib-conjugates are typically given at 10 µg/dose, lower doses (typically fractions e.g. ½, ⅓, ¼, etc.) have been used [4, 6]. In ref. 6, for example, Hib-conjugates were administered at 5 µg/dose or 3.33 µg/dose.

The same approach has been extended to Hib-conjugates within DTP-Hib vaccines. For example, reference 8 compares full-dose, half-dose and third-dose use of Hib-conjugate in combination with a DTwP vaccine and, although geometric mean concentrations of anti-PRP bodies were reduced in patients receiving combined DTP-Hib vaccines compared to separate administration of DTP and Hib, acceptable protective anti-Hib immune responses were seen in all cases. Reference 9 uses a 10-fold dilution of Hib-conjugate dosage by reconstituting a single Hib dose with a ten-dose vial of DTwP. Reference 10 discloses reconstitution of lyophilised Hib-conjugate at full dose, half-dose or quarter-dose using the TRITANRIX™ DTwP-HBsAg vaccine.

In each of these cases, however, the Hib-conjugate was in lyophilised form and had to be reconstituted by aqueous DTP antigens prior to administration. These vaccines must thus be provided in two separate containers (aqueous DTP in one, lyophilised Hib in the other), and this double container requirement imposes additional cost and logistical requirements at the packaging stage, the transport stage, the storage stage and the administration stage. As the reduced-dose vaccines are intended to reduce cost and encourage distribution in the developing world then these additional requirements are significant disadvantages. The requirement for a reconstitution step also means that there is a risk of error by the end user, a tendency towards non-standardised dosages, a risk of contamination of the mixed product and a need to train staff in the reconstitution procedure. All of these problems frustrate the intended target market i.e. the developing world.

There thus remains a need for a combination vaccine that includes a low dose of Hib-conjugate antigen and does not need separate packaging of the Hib antigen.

DISCLOSURE OF THE INVENTION

The invention provides a combination vaccine comprising antigens for protecting a subject against at least diphtheria ('D'), tetanus ('T'), pertussis ('P') and *H. influenzae* type b ('Hib'), wherein: (a) the antigen for protecting against Hib is a conjugate of a Hib capsular saccharide; (b) the concentration of the Hib conjugate in the vaccine is <15 µg/ml; and (c) the Hib conjugate has never been lyophilised. Vaccines of the invention have been found to be safe and to be highly immunogenic when compared to the immune responses observed in references 6, 8 and 9.

The invention also provides a combination vaccine comprising antigens for protecting a subject against at least diphtheria ('D'), tetanus ('T'), pertussis ('P') and *H. influenzae* type b wherein: (a) the antigen for protecting against Hib is a conjugate of a Hib capsular saccharide; (b) the concentration of the Hib conjugate in the vaccine is <15 µg/ml; and (c) the vaccine (i) does not contain an aluminium hydroxide adjuvant and/or (ii) does not contain an aluminium potassium sulfate adjuvant. Aluminium hydroxide is believed to be involved in degradation of Hib saccharide conjugates, and so as an adjuvant the vaccine preferably includes an aluminium phosphate adjuvant instead. Where an aluminium adjuvant (e.g. an aluminium phosphate adjuvant) is present, it is preferred that the Hib conjugate is not adsorbed to it.

The invention also provides a vial having a piercable seal and containing a combination vaccine, which combination vaccine comprises antigens for protecting a subject against at least diphtheria, tetanus, pertussis and *H. influenzae* type b ('Hib'), wherein the antigen for protecting against Hib is a conjugate of a Hib capsular saccharide, and wherein: (a) the concentration of the Hib conjugate in the vaccine is <15 µg/ml, and (b) the vial's piercable seal has not been pierced.

The invention also provides a hermetically-sealed container containing a combination vaccine comprising antigens for protecting a subject against at least diphtheria, tetanus, pertussis and *H. influenzae* type b ('Hib'), wherein the antigen for protecting against Hib is a conjugate of a Hib capsular saccharide, and wherein the concentration of the Hib conjugate in the vaccine is <15 µg/ml.

The invention also provides a process for preparing a combination vaccine comprising antigens for protecting a subject against at least diphtheria ('D'), tetanus ('T'), pertussis ('P') and *H. influenzae* type b ('Hib'), wherein the antigen for protecting against Hib is a conjugate of a Hib capsular saccharide and the concentration of Hib conjugate in the vaccine is <15 µg/ml, and wherein (a) the process comprises a step of admixing said antigens for protecting against D, T, P and Hib, and (b) the process (i) does not include a step of lyophilisation of the Hib conjugate antigen, and/or (ii) does not include a step of packaging the diphtheria, tetanus and pertussis antigens in admixed form separately from the Hib conjugate antigen.

The invention also provides a process for inserting a combination vaccine into a container, wherein: (a) the vaccine comprises antigens for protecting a subject against at least diphtheria, tetanus, pertussis and *H. influenzae* type b ('Hib'); (b) the antigen for protecting against Hib is a conjugate of a Hib capsular saccharide; and (c) the concentration of the Hib conjugate in the vaccine is <15 µg/ml.

The invention also provides a process for attaching a label to a container, wherein: (a) the container contains a combination vaccine that comprises antigens for protecting a subject against at least diphtheria, tetanus, pertussis and *H. influenzae* type b ('Hib'); (b) the antigen for protecting against Hib is a conjugate of a Hib capsular saccharide; and (c) the concentration of the Hib conjugate in the vaccine is <15 µg/ml. The label may indicate that the container contains a vaccine.

The invention also provides a process for inserting a combination vaccine into a container and then extracting the vaccine from the container, wherein: (a) the vaccine comprises antigens for protecting a subject against at least diphtheria, tetanus, pertussis and *H. influenzae* type b ('Hib'); (b) the antigen for protecting against Hib is a conjugate of a Hib capsular saccharide; and (c) the concentration of the Hib conjugate in the vaccine is <15 µg/ml.

DTP Components

The diphtheria antigen is preferably a diphtheria toxoid. The preparation of diphtheria toxoids is well documented [e.g. chapter 13 of reference 11]. Any suitable diphtheria toxoid may be used. The concentration of diphtheria toxoid is generally between 5 and 100 Lf/ml. A preferred concentration is between 10 and 50 Lf/ml. A more preferred concentration is between 20 and 40 Lf/ml. Most preferably, the concentration is about 30 Lf/ml. As an alternative, a preferred concentration is between 5 and 25 Lf/ml, a more preferred concentration is between 10 and 20 Lf/ml, and a most preferred concentration is about 15 Lf/ml. Where an acellular pertussis antigen is used, however, then a preferred concentration for the diphtheria toxoid is about 50 Lf/ml.

The tetanus antigen is preferably a tetanus toxoid. The preparation of tetanus toxoids is well documented [e.g. chapter 27 of reference 11]. Any suitable tetanus toxoid may be used. The concentration of tetanus toxoid is generally between 1 and 50 Lf/ml. A preferred concentration is between 2 and 9 Lf/ml. A more preferred concentration is between 5 and 8 Lf/ml. Most preferably, the concentration is about 6.5 Lf/ml. Where an acellular pertussis antigen is used, however, then a preferred concentration for the diphtheria toxoid is about 20 Lf/ml.

The pertussis antigen used according to the invention may be cellular (e.g. whole cell) or acellular. The preparation of both types of antigen is well documented [e.g. see chapter 21 of reference 11; see also reference 12]. For cellular pertussis antigens, the concentration of pertussis antigens is generally between 5 and 50 OU/ml. A preferred concentration is between 10 and 40 OU/ml. A more preferred concentration is between 25 and 35 OU/ml. Most preferably, the concentration is about 30 OU/ml. Where acellular antigens are used, it is preferred to use pertussis holotoxin (PT) and filamentous haemagglutinin (FHA), more preferably combined with pertactin (also known as PRN or 69 kDa antigen) and, optionally, agglutinogens (also known as fimbriae) 2 and 3 [13]. Typical levels of pertussis antigens per vaccine dose (e.g. per 0.5 ml) are: 10 µg PT, 5 µg FHA, 3 µg or 5 µg PRN, 5 µg combined fimbriae. PT is a toxic protein and, when present in the pertussis antigen, it is preferably detoxified. Detoxification may be by chemical and/or genetic means. A preferred detoxified mutant is the 9K/129 G double mutant [14].

The Hib Conjugate

The *H. influenzae* type B antigen used in vaccines of the invention comprises a Hib capsular saccharide antigen. Saccharide antigens from *H. influenzae* b are well known [e.g. chapter 14 of ref. 11]. The Hib saccharide is conjugated to a carrier protein in order to enhance its immunogenicity, especially in children. The preparation of Hib capsular saccharide is well documented [e.g. references 15 to 24]. The invention may use any suitable Hib conjugate. Suitable carrier proteins are described above, and preferred carriers for Hib saccharides are $CRM_{197}$ ('HbOC'), tetanus toxoid ('PRP-T') and the outer membrane complex of *N. meningitidis* ('PRP-OMP').

The saccharide moiety of the conjugate may be a polysaccharide (e.g. full-length polyribosylribitol phosphate (PRP)), but it is preferred to use oligosaccharides (e.g. MW from ~1 to ~5 kDa). These are conveniently formed by fragmentation of purified PRP (e.g. by hydrolysis), which will usually be followed by purification of the fragments of the desired size. Where the composition of the invention includes a conjugated oligosaccharide, oligosaccharide preparation should precede conjugation.

Preferred carrier proteins for covalent conjugation are bacterial toxins or toxoids, such as diphtheria toxoid or tetanus toxoid. The $CRM_{197}$ diphtheria toxin mutant [25-27] is particularly preferred. Other suitable carrier proteins include the *N. meningitidis* outer membrane protein [28], synthetic peptides [29, 30], heat shock proteins [31, 32], pertussis proteins [33, 34], cytokines [35], lymphokines [35], hormones [35], growth factors [35], artificial proteins comprising multiple human $CD4^+$ T cell epitopes from various pathogen-derived antigens [36], protein D from *H. influenzae* [37, 38], pneumococcal surface protein PspA [39], iron-uptake proteins [40], toxin A or B from *C. difficile* [41], etc. Preferred carriers are diphtheria toxoid, tetanus toxoid and $CRM_{197}$.

Conjugates with a saccharide:protein ratio (w/w) of between 1:5 (i.e. excess protein) and 5:1 (i.e. excess saccharide) may be used e.g. ratios between 1:2 and 5:1 and ratios between 1:1.25 and 1:2.5.

Conjugates may be used in conjunction with free carrier protein [42]. When a given carrier protein is present in both free and conjugated form in a composition of the invention, the unconjugated form is preferably no more than 5% of the total amount of the carrier protein in the composition as a whole, and more preferably present at less than 2% by weight.

Any suitable conjugation reaction can be used, with any suitable linker where necessary.

The saccharide will typically be activated or functionalised prior to conjugation. Activation may involve, for example, cyanylating reagents such as CDAP (e.g. 1-cyano-4-dimethylamino pyridinium tetrafluoroborate [43, 44, etc.]). Other suitable techniques use carbodiimides, hydrazides, active esters, norborane, p-nitrobenzoic acid, N-hydroxysuccinimide, S-NHS, EDC, TSTU; see also the introduction to reference 22).

Linkages via a linker group may be made using any known procedure, for example, the procedures described in references 45 and 46. One type of linkage involves reductive amination of the polysaccharide, coupling the resulting amino group with one end of an adipic acid linker group, and then coupling a protein to the other end of the adipic acid linker group [20, 47, 48]. Other linkers include B-propionamido [49], nitrophenyl-ethylamine [50], haloacyl halides [51], glycosidic linkages [52], 6-aminocaproic acid [53], ADH [54], $C_4$ to $C_{12}$ moieties [55] etc. As an alternative to using a linker, direct linkage can be used. Direct linkages to the protein may comprise oxidation of the polysaccharide followed by reductive amination with the protein, as described in, for example, references 56 and 57.

A process involving the introduction of amino groups into the saccharide (e.g. by replacing terminal =O groups with —NH$_2$) followed by derivatisation with an adipic diester (e.g. adipic acid N-hydroxysuccinimido diester) and reaction with carrier protein is preferred. Another preferred reaction uses CDAP activation with a protein D carrier.

After conjugation, free and conjugated saccharides can be separated. There are many suitable methods for this separation, including hydrophobic chromatography, tangential ultrafiltration, diafiltration, etc. [see also refs. 58 & 59, etc.]. If a vaccine comprises a given saccharide in both free and conjugated forms, the unconjugated form is preferably no more than 20% by weight of the total amount of that saccharide in the composition as a whole (e.g. ≤15%, ≤10%, ≤5%, ≤2%, ≤1%).

A preferred conjugate comprises a Hib oligosaccharide covalently linked to CRM$_{197}$ via an adipic acid linker [60, 61]. Tetanus toxoid is also a preferred carrier.

Administration of the Hib antigen preferably results in an anti-PRP antibody concentration of ≥0.15 µg/ml, and more preferably ≥1 µg/ml. These are the standard acceptable response thresholds.

The concentration of Hib conjugate in vaccines of the invention is <15 µg/ml e.g. ≤14 µg/ml, ≤12 µg/ml, ≤10 µg/ml, ≤7.5 µg/ml, ≤5 µg/ml, ≤4 µg/ml, ≤3 µg/ml, ≤2 µg/ml, ≤1 µg/ml, etc. Where the carrier protein is not OMPC then it is possible to use slightly higher doses e.g. <20 µg/ml, ≤19 µg/ml, ≤18 µg/ml, ≤17 µg/ml, ≤16 µg/ml, etc. The concentration of Hib conjugate in vaccines of the invention will generally, however, be at least 0.1 µg/ml e.g. ≥0.2 µg/ml, ≥0.3 µg/ml, ≥0.4 µg/ml, ≥0.5 µg/ml, ≥0.6 µg/ml, ≥0.7 µg/ml, ≥0.8 µg/ml, ≥0.9 µg/ml, ≥1.0 µg/ml, ≥1.25 µg/ml, ≥1.5 µg/ml, ≥2.0 µg/ml, ≥3.5 µg/ml, etc. Thus preferred ranges for the concentration of Hib conjugate in the vaccines are from $d_1$ to $d_2$ µg/ml, where: (i) $d_1$<$d_2$; (ii) $d_1$ is selected from 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.25, 2.5, 2.75, 3.0, 3.5 and 4.0; and (iii) $d_2$ is selected from 1, 2, 3, 4, 5, 6, 7, 8, 9, 10, 11, 12, 13, 14 and 15.

Concentrations of Hib conjugates are defined in the description and the claims in terms of mass of saccharide (i.e. the dose of the conjugate (carrier+saccharide) as a whole is higher than the stated dose) in order to avoid variation due to choice of carrier.

Hib conjugate antigens in compositions of the invention are not and have never been lyophilised.

Adjuvants

Aluminium hydroxide is believed to be involved in degradation of Hib saccharide conjugates [62], and so as an adjuvant the vaccine preferably includes an aluminium phosphate adjuvant instead.

Where an aluminium phosphate adjuvant is present, it is preferred that the Hib conjugate is not adsorbed to it, in contrast to reference 63. Non-adsorption can be achieved during manufacture by selection of the correct mixing order, by selecting an appropriate pH during antigen/adjuvant mixing, and/or by choosing an adjuvant with an appropriate point of zero charge (PZC) [64] (see below).

Where aluminium phosphate is present, diphtheria toxoid will typically be adsorbed onto aluminium phosphate. It is preferred that adsorption is partial e.g. of the total diphtheria toxoid in the composition, about 30-80% by weight is adsorbed (e.g. about 40%-70%, about 50%-60% etc.). Adsorption of diphtheria toxoid rises over time when stored at about 37° C. Tetanus toxoid will typically be adsorbed onto aluminium phosphate. It is preferred that adsorption is partial e.g. of the total tetanus toxoid in the composition, no more than 40% by weight is adsorbed (e.g. no more than 30%, no more than 20%, no more than 10% etc.). Levels of tetanus toxoid adsorption may be about 0%. Hib-conjugate remains un-adsorbed to aluminium adjuvant. It is preferred that no more than 15% by weight of Hib-conjugate in the composition should be adsorbed to aluminium phosphate (e.g. at most 10%, at most 5%, at most 4%, at most 3%, at most 2%, or at most 1%).

The term "aluminium phosphate" as used herein includes aluminium phosphate, aluminium hydroxyphosphate and aluminium hydroxyphosphate sulfate. The preferred form of aluminium phosphate for use with the present invention is a hydroxyphosphate salt.

The PO$_4$/Al$^{3+}$ molar ratio of the aluminium phosphate will generally be between 0.3 and 1.2, preferably between 0.8 and 1.2, and more preferably 0.95±0.1. A typical adjuvant is amorphous aluminium hydroxyphosphate with PO$_4$/Al molar ratio between 0.84 and 0.92, included at 0.6 mg Al$^{3+}$/ml. The aluminium phosphate will generally be amorphous, particularly for hydroxyphosphate salts. The aluminium phosphate will generally be particulate. Typical diameters of the particles are in the range 0.5-20 µm (e.g. about 5-10 µm) after any antigen adsorption.

The PZC of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 5.0 and 7.0, more preferably between 5.5 and 6.0 e.g. about 5.7.

The aluminium phosphate is preferably used in the form of an aqueous solution to which antigens are added (NB: it is standard to refer to aqueous aluminium phosphate as a "solution" although, on a strict physicochemical view, the salt is insoluble and forms a suspension). It is preferred to dilute the aluminium phosphate to the required concentration and to ensure a homogenous solution before the addition of the antigenic components.

The concentration of Al$^{3+}$ prior to addition of antigens is generally between 0 and 10 mg/ml. A preferred concentration is between 2 and 6 mg/ml. A more preferred concentration is between 4 and 5 mg/ml e.g. 4.4 mg/ml (corresponding to aluminium phosphate concentration of 20 mg/ml). The concentration of Al$^{3+}$ in final vaccines of the invention is generally between 0.1 and 2.0 mg/ml. A preferred concentration is between 0.2 and 1.5 mg/ml. A more preferred concentration is between 0.3 and 1.0 mg/ml. Most preferably, the concentration is about 0.6 mg/ml.

An aluminium phosphate solution used to prepare a vaccine of the invention may contain a buffer (e.g. a phosphate or a histidine buffer), but this is not necessary. The aluminium phosphate solution is preferably sterile and pyrogen-free. The aluminium phosphate solution may include free aqueous phosphate ions e.g. present at a concentration between 1.0 and 20 mM, preferably between 5 and 15 mM, and more preferably about 10 mM. The aluminium phosphate solution may also comprise sodium chloride. The concentration of sodium chloride is preferably in the range of 0.1 to 100 mg/ml (e.g. 0.5-50 mg/ml, 1-20 mg·ml, 2-10 mg/ml) and is more preferably about 3±1 mg/ml. The presence of NaCl facilitates the correct measurement of pH prior to adsorption of antigens.

Although the use of aluminium salts as sole adjuvants is normal, other adjuvants which may be included in vaccines of the invention include, but are not limited to:

A. Mineral-Containing Compositions

Mineral containing compositions suitable for use as adjuvants in the invention include mineral salts, such as aluminium salts and calcium salts. The invention includes mineral salts such as hydroxides (e.g. oxyhydroxides), phosphates (e.g. hydroxyphosphates, orthophosphates), sulphates, etc. [e.g. see chapters 8 & 9 of ref. 65], or mixtures of different mineral compounds, with the compounds taking any suitable form (e.g. gel, crystalline, amorphous, etc.), and with adsorption being preferred. The mineral containing compositions may also be formulated as a particle of metal salt [66].

Vaccine compositions of the invention are preferably substantially free of aluminium hydroxides (e.g. aluminium oxyhydroxides). The concentration of aluminium hydroxides in the composition will usually be less than 100 μg/ml, preferably less than 50 μg/ml, more preferably less than 10 μg/ml, and most preferably less than 1 μg/ml. In particular, the Hib-conjugate antigen is preferably not adsorbed onto an aluminium hydroxide.

A calcium phosphate adjuvant may be used.

B. Oil Emulsions

Oil emulsion compositions suitable for use as adjuvants in the invention include squalene-water emulsions, such as MF59 [Chapter 10 of ref. 65; see also ref. 67] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

C. Saponin Formulations [Chapter 22 of Ref 65]

Saponin formulations may also be used as adjuvants in the invention. Saponins are a heterologous group of sterol glycosides and triterpenoid glycosides that are found in the bark, leaves, stems, roots and even flowers of a wide range of plant species. Saponin from the bark of the *Quillaia saponaria* Molina tree have been widely studied as adjuvants. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref 68. Saponin formulations may also comprise a sterol, such as cholesterol [69].

Combinations of saponins and cholesterols can be used to form unique particles called immunostimulating complexes (ISCOMs) [chapter 23 of ref 65]. ISCOMs typically also include a phospholipid such as phosphatidylethanolamine or phosphatidylcholine. Any known saponin can be used in ISCOMs. Preferably, the ISCOM includes one or more of QuilA, QHA and QHC. ISCOMs are further described in refs. 69-71. Optionally, the ISCOMS may be devoid of additional detergent [72].

A review of the development of saponin based adjuvants can be found in refs. 73 & 74.

D. Virosomes and Virus-Like Particles

Virosomes and virus-like particles (VLPs) can also be used as adjuvants in the invention. These structures generally contain one or more proteins from a virus optionally combined or formulated with a phospholipid. They are generally non-pathogenic, non-replicating and generally do not contain any of the native viral genome. The viral proteins may be recombinantly produced or isolated from whole viruses. These viral proteins suitable for use in virosomes or VLPs include proteins derived from influenza virus (such as HA or NA), Hepatitis B virus (such as core or capsid proteins), Hepatitis E virus, measles virus, Sindbis virus, Rotavirus, Foot-and-Mouth Disease virus, Retrovirus, Norwalk virus, human Papilloma virus, HIV, RNA-phages, Qβ-phage (such as coat proteins), GA-phage, fr-phage, AP205 phage, and Ty (such as retrotransposon Ty protein p1). VLPs are discussed further in refs. 75-80. Virosomes are discussed further in, for example, ref. 81

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3 dMPL). 3 dMPL is a mixture of 3 de-O-acylated monophosphoryl lipid A with 4, 5 or 6 acylated chains. A preferred "small particle" form of 3 De-O-acylated monophosphoryl lipid A is disclosed in ref. 82. Such "small particles" of 3 dMPL are small enough to be sterile filtered through a 0.22 μm membrane [82]. Other non-toxic LPS derivatives include monophosphoryl lipid A mimics, such as aminoalkyl glucosaminide phosphate derivatives e.g. RC-529 [83, 84].

Lipid A derivatives include derivatives of lipid A from *Escherichia coli* such as OM-174. OM-174 is described for example in refs. 85 & 86.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 87, 88 and 89 disclose possible analog substitutions e.g. replacement of guanosine with T-deoxy-7-deazaguanosine. The adjuvant effect of CpG oligonucleotides is further discussed in refs. 90-95.

The CpG sequence may be directed to TLR9, such as the motif GTCGTT or TTCGTT [96]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 97-99. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 96 & 100-102.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref. 103 and as parenteral adjuvants in ref. 104. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivaties thereof, particularly LT-K63 and LT-R72, as adjuvants can be found in refs. 105-112. Numerical reference for amino acid substitutions is preferably based on the alignments of the A and B subunits of ADP-ribosylating toxins set forth in ref. 113, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [114], etc.) [115], interferons (e.g. interferon-γ), macrophage colony stimulating factor, and tumor necrosis factor.

G. Bioadhesives and Mucoadhesives.

Bioadhesives and mucoadhesives may also be used as adjuvants in the invention. Suitable bioadhesives include esterified hyaluronic acid microspheres [116] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [117].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes (Chapters 13 & 14 of Ref 65)

Examples of liposome formulations suitable for use as adjuvants are described in refs. 118-120.

J. Polyoxyethylene Ether and Polyoxyethylene Ester Formulations

Adjuvants suitable for use in the invention include polyoxyethylene ethers and polyoxyethylene esters [121]. Such formulations further include polyoxyethylene sorbitan ester surfactants in combination with an octoxynol [122] as well as polyoxyethylene alkyl ethers or ester surfactants in combination with at least one additional non-ionic surfactant such as an octoxynol [123]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Polyphosphazene (PCPP)

PCPP formulations are described, for example, in refs. 124 and 125.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquamod and its homologues (e.g. "Resiquimod 3M"), described further in refs. 126 and 127.

The invention may also comprise combinations of aspects of one or more of the adjuvants identified above. For example, the following adjuvant compositions may be used in the invention: (1) a saponin and an oil-in-water emulsion [128]; (2) a saponin (e.g. QS21)+a non-toxic LPS derivative (e.g. 3 dMPL) [129]; (3) a saponin (e.g. QS21)+a non-toxic LPS derivative (e.g. 3 dMPL)+a cholesterol; (4) a saponin (e.g. QS21)+3 dMPL+IL-12 (optionally+a sterol) [130]; (5) combinations of 3 dMPL with, for example, QS21 and/or oil-in-water emulsions [131]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3 dMPL).

Other substances that act as immunostimulating agents are disclosed in chapter 7 of ref. 65.

Further Antigens

Compositions of the invention contain D, T, P and Hib antigens. They may also include further antigens, such as:

a saccharide antigen from N. meningitidis serogroup A, C, W135 and/or Y, such as the oligosaccharide disclosed in ref. 132 from serogroup C or the oligosaccharides of ref. 133. The vaccine preferably contains conjugates from 2, 3 or 4 of serogroups A, C, W135 and Y.

a saccharide antigen from *Streptococcus pneumoniae* [e.g. refs. 134 to 136].

an antigen from hepatitis A virus, such as inactivated virus [e.g. 137, 138].

an antigen from hepatitis B virus, such as the surface and/or core antigens [e.g. 138, 139].

an outer-membrane vesicle (OMV) or bleb preparation from N. meningitidis serogroup B, such as those disclosed in refs. 140, 141, 142, 143, etc.

a protein antigen from N. meningitidis serogroup B, such as those in refs. 144 to 150, with protein '287' (see below) and derivatives (e.g. 'ΔG287') being particularly preferred.

polio antigen(s) [e.g. 151, 152] such as IPV.

The composition may comprise one or more of these further antigens. Antigens will typically be present at a concentration of at least 1 μg/ml each. In general, the concentration of any given antigen will be sufficient to elicit an immune response against that antigen. It is preferred that the protective efficacy of individual saccharide antigens is not removed by combining them, although actual immunogenicity (e.g. ELISA titres) may be reduced.

Where a saccharide antigen is used, it is preferably conjugated to a carrier protein in order to enhance immunogenicity.

As an alternative to using protein antigens in the composition of the invention, nucleic acid encoding the antigen may be used [e.g. refs. 153 to 161]. Protein components of the compositions of the invention may thus be replaced by nucleic acid (preferably DNA e.g. in the form of a plasmid) that encodes the protein. Similarly, compositions of the invention may comprise proteins which mimic saccharide antigens e.g. mimotopes [162] or anti-idiotype antibodies.

These may replace individual saccharide components, or may supplement them. As an example, the vaccine may comprise a peptide mimic of the MenC [163] or the MenA [164] capsular polysaccharide in place of the saccharide itself.

Where a vaccine of the invention includes a hepatitis B surface antigen ('HBsAg'), this antigen can be made in two ways. The first method involves purifying the antigen in particulate form from the plasma of chronic hepatitis B carriers, as large quantities of HBsAg are synthesized in the liver and released into the blood stream during an HBV infection. The second way is preferred and involves expressing the protein by recombinant DNA methods. It is preferred that the HBsAg is prepared by expression in the *Saccharomyces cerevisiae* yeast. The HBsAg gene may be inserted into a plasmid, and its expression from the plasmid may be controlled by a promoter such as the 'GAPDH' promoter (from the glyceraldehyde-3-phosphate dehydrogenase gene). The yeast may be cultured in a synthetic medium. HBsAg can then be purified by a process involving steps such as precipitation, ion exchange chromatography, and ultrafiltration. After purification, HBsAg may be subjected to dialysis (e.g. with cysteine). The HBsAg may be used in a particulate form.

Where a vaccine of the invention includes a polio antigen, it is preferred to use three poliovirus antigens—poliovirus Type 1 (e.g. Mahoney strain), poliovirus Type 2 (e.g. MEF-1 strain), and poliovirus Type 3 (e.g. Saukett strain). Polioviruses may be grown in cell culture. A preferred culture uses a VERO cell line, which is a continuous cell line derived from monkey kidney. VERO cells can conveniently be cultured microcarriers. Culture of the VERO cells before and during viral infection may involve the use of bovine-derived material, such as calf serum, and this material should be obtained from sources which are free from bovine spongiform encephalitis (BSE). Culture may also involve materials such as lactalbumin hydrolysate. After growth, virions may be purified using techniques such as ultrafiltration, diafiltration, and chromatography. Prior to administration to patients, the viruses must be inactivated, and this can be achieved by treatment with formaldehyde. Viruses are preferably grown, purified and inactivated individually, and are then combined to give a bulk mixture for addition to the adsorbed diphtheria and tetanus antigens.

Antigens in vaccines of the invention will be present in 'immunologically effective amounts' i.e. the administration of that amount to an individual, either in a single dose or as part of a series, is effective for treatment or prevention of disease. This amount varies depending upon the health and physical condition of the individual to be treated, age, the taxonomic group of individual to be treated (e.g. human, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Dosage treatment may be a single dose schedule or a multiple dose schedule (e.g. including booster doses).

Non-Immunological Components of Vaccines of the Invention

Vaccines of the invention will typically, in addition to the antigenic and adjuvant components mentioned above, comprise one or more 'pharmaceutically acceptable carriers', which include any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose [165], trehalose [166], lactose, and lipid aggregates (such as oil droplets or liposomes). Such carriers are well known to those of ordinary skill in the art. The vaccines may also contain diluents, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier. A thorough discussion of pharmaceutically acceptable excipients is available in reference 167.

Compositions of the invention are in aqueous form i.e. solutions or suspensions. Liquid formulation of this type allows the compositions to be administered direct from their packaged form, without the need for reconstitution in an aqueous medium, and are thus ideal for injection. Compositions may be presented in vials, or they may be presented in ready-filled syringes. The syringes may be supplied with or without needles. A syringe will include a single dose of the composition, whereas a vial may include a single dose or multiple doses.

Liquid vaccines of the invention are also suitable for reconstituting other vaccines from a lyophilised form. Where a vaccine is to be used for such extemporaneous reconstitution, the invention provides a kit, which may comprise two vials, or may comprise one ready-filled syringe and one vial, with the contents of the syringe being used to reactivate the contents of the vial prior to injection.

Vaccines of the invention may be packaged in unit dose form or in multiple dose form. For multiple dose forms, vials are preferred to pre-filled syringes. Effective dosage volumes can be routinely established, but a typical human dose of the composition for injection has a volume of 0.5 ml.

Vaccines of the invention generally have a pH of between 6.0 and 8.0, more preferably between 6.3 and 6.9 e.g. 6.6±0.2. Vaccines are preferably buffered at this pH. Stable pH may be maintained by the use of a buffer. If a composition comprises an aluminium hydroxide salt, it is preferred to use a histidine buffer [168]. The composition may be sterile and/or pyrogen-free. Aluminium phosphate and whole cell pertussis antigens are incompatible with filter sterilisation and so, when a composition of the invention includes one of these components, it is preferred to sterilise the composition of the invention by autoclaving and/or to use sterile components in its production.

Compositions of the invention may be isotonic with respect to humans.

Vaccines of the invention may include an antimicrobial, particularly when packaged in multiple dose format. Many antimicrobials are mercury-based (e.g. thiomersal), although mercurial preservatives are preferably avoided e.g. 2-phenoxyethanol may be used. Any preservative is preferably present at low levels (e.g. 0.01% by volume). Preservative may be added exogenously and/or may be a component of the bulk antigens which are mixed to form the composition (e.g. present as a preservative in pertussis antigens).

Vaccines of the invention may comprise detergent e.g. a Tween (polysorbate), such as Tween 80. Detergents are generally present at low levels e.g. <0.01%.

Vaccines of the invention may include sodium salts (e.g. sodium chloride) to give tonicity. The composition may comprise sodium chloride. The concentration of sodium chloride in the composition is preferably in the range of 0.1 to 100 mg/ml (e.g. 1-50 mg/ml, 2-20 mg/ml, 5-15 mg/ml) and is more preferably 10±2 mg/ml NaCl e.g. about 9 mg/ml.

Vaccines of the invention will generally include a buffer. A phosphate or histidine buffer is typical.

Vaccines of the invention may include free phosphate ions in solution (e.g. by the use of a phosphate buffer) in order to favour non-adsorption of antigens. The concentration of free phosphate ions in the composition of the invention is generally between 0.1 and 10.0 mM, preferably between 1 and 5 mM, and more preferably about 2.5 mM.

Packaging of Vaccines of the Invention

Vaccines of the invention can be packaged in various types of container e.g. in vials, in syringes, etc.

For prior art DTP-Hib vaccines that require reconstitution of a lyophilised Hib component, aqueous DTP antigens are drawn from a first sealed vial into a syringe and are then introduced into a second sealed vial that contains the lyophilised material. The reconstituted vaccine is then withdrawn into the same syringe for administration to a patient. In contrast, Hib conjugates in vaccines of the invention are stable in aqueous conditions and do not require lyophilisation. The invention is thus able to provide a vial having a piercable seal and containing a DTP-Hib vaccine, wherein the piercable seal has not been pierced. Similarly, the invention is able to provide a hermetically sealed container containing a vaccine of the invention.

Prior art DTP-Hib vaccines that require reconstitution of a lyophilised Hib component must be packaged into two separate containers. In contrast, the invention allows the provision of a process for inserting a vaccine of the invention into a container in a form that already includes DTP-Hib antigens. The insertion is preferably not through a seal in the container.

Similarly, as vaccine packaging is labelled during manufacture then prior art vaccines DTP-Hib are labelled while they are in separate DTP and Hib formats, whereas the invention allows labelling of the vaccine in its final DTP-Hib format.

Furthermore, prior art reconstituted DTP-Hib vaccines are withdrawn from their containers in DTP-Hib form but they are not inserted into the containers in that form. According to the invention, however, such DTP-Hib vaccines can be both inserted and extracted in the admixed DTP-Hib form. The time between insertion and extraction can be at least n weeks, where n is selected from 1, 2, 3, 4, 5, 6, 7, 8, 9, 10, 15, 20, 25 or more. Extraction will generally be via the needle (e.g. the needle of a sterile delivery device, such as a syringe), although insertion into the container will usually be from a manufacturing line rather than from a delivery device.

Preparing Vaccines of the Invention

Vaccines of the invention contain at least DTP-Hib antigens, and their preparation thus involves admixing these four antigens. Unlike the preparation of reconstituted prior art DTP-Hib vaccines, the invention can provide a preparation process that does not include a step of lyophilisation of the Hib conjugate. Similarly, the invention is able to provide a preparation process that does not include a step of packaging admixed DTP antigens separately from Hib antigen.

During preparation, antigens which are added are generally not already adsorbed onto an aluminium salt (i.e. they are not 'pre-adsorbed'). It is thus preferred that, for each of the antigens which is added, no more than 5% by weight (preferably none) is already adsorbed to an aluminium salt (e.g. at most 4%, at most 3%, or at most 2%). In some situations, however, pre-adsorbed antigens may be added.

A typical process for preparing bulk vaccine of the invention will add the Hib component to a mixture of the D, T and P components i.e. the DTP components are mixed prior to addition of the Hib component. This order of mixing allows the ionic strength and/or pH of the composition to be adjusted (e.g. pH<7) prior to addition of the Hib component in order to prevent adsorption to any aluminium adjuvant that may be present.

Vaccines of the invention are preferably prepared at between 15° C. and 30° C. (e.g. between 19° C. and 27° C., or at 23±4° C.).

Administration of Vaccines of the Invention

The invention provides a method for raising an antibody response in a mammal, comprising administering a vaccine of the invention to the mammal. The vaccines can be administered prophylactically (i.e. to prevent infection) or therapeutically (i.e. to treat disease after infection).

The invention provides a method for raising an immune response in a mammal, comprising the step of administering an effective amount of a vaccine of the invention. The immune response is preferably protective and preferably involves antibodies. The method may raise a booster response.

The mammal is preferably a human. Where the vaccine is for prophylactic use, the human is preferably a child (e.g. a toddler or infant) or a teenager; where the vaccine is for therapeutic use, the human is preferably an adult. A vaccine intended for children may also be administered to adults e.g. to assess safety, dosage, immunogenicity, etc.

The invention also provides compositions of the invention for use as a medicament. The medicament is preferably able to raise an immune response in a mammal (i.e. it is an immunogenic composition) and is more preferably a vaccine.

The invention also provides the use of at least diphtheria, tetanus, pertussis and *H. influenzae* type b ('Hib') antigens in the manufacture of a combined vaccine for the immunisation of a patient, wherein (a) the antigen for protecting against Hib is a conjugate of a Hib capsular saccharide; (b) the concentration of the Hib conjugate in the vaccine is <15 μg/ml; and (c) the manufacture does not include lyophilisation of the Hib conjugate.

These uses and methods are preferably for the prevention and/or treatment of *C. diphtheriae, C. tetani, B. pertussis* and *H. influenzae* infections and of disease caused by these infections e.g. the prevention of diphtheria, of tetanus, of whooping cough, of bacterial meningitis, etc.

One way of checking efficacy of therapeutic treatment involves monitoring bacterial infection after administration of the composition of the invention. One way of checking efficacy of prophylactic treatment involves monitoring immune responses against the antigens after administration of the composition. Immunogenicity of compositions of the invention can be determined by administering them to test subjects (e.g. children 12-16 months age, or animal models [169]) and then determining standard immunological parameters. These immune responses will generally be determined around 4 weeks after administration of the composition, and compared to values determined before administration of the composition. Rather than assess actual protective efficacy in patients, standard animal and in vitro models and correlates of protection for assessing the efficacy of Hib and DTP vaccines are well known.

Compositions of the invention will generally be administered directly to a patient. Direct delivery may be accomplished by parenteral injection (e.g. subcutaneously, intraperitoneally, intravenously, intramuscularly, or to the interstitial space of a tissue), or by rectal, oral, vaginal, topical, transdermal, intranasal, ocular, aural, pulmonary or other mucosal administration. Intramuscular administration to the thigh or the upper arm is preferred. Injection may be via a needle (e.g. a hypodermic needle), but needle-free injection may alternatively be used. A typical intramuscular dose is 0.5 ml.

The invention may be used to elicit systemic and/or mucosal immunity.

Dosage treatment can be a single dose schedule or a multiple dose schedule. Multiple doses may be used in a primary immunisation schedule and/or in a booster immunisation schedule. A primary dose schedule may be followed by a booster dose schedule. Suitable timing between priming doses (e.g. between 4-16 weeks), and between priming and boosting, can be routinely determined.

Bacterial infections affect various areas of the body and so the compositions of the invention may be prepared in various forms. For example, the compositions may be prepared as injectables, either as liquid solutions or suspensions. The composition may be prepared for pulmonary administration e.g. as an inhaler, using a fine powder or a spray. The composition may be prepared as a suppository or pessary. The composition may be prepared for nasal, aural or ocular administration e.g. as spray, drops, gel or powder [e.g. refs 170 & 171]. Successful intranasal administration of Hib saccharides [172] and DTP vaccines [173, 174] has been reported.

General

The term "comprising" encompasses "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

MODES FOR CARRYING OUT THE INVENTION

Four DTwP-Hib vaccine formulations were prepared, differing only in their dose of Hib-CRM$_{197}$ conjugate. Vaccines were prepared as 0.5 ml doses with the following antigenic compositions:

| | A | B | C | D [175] |
|---|---|---|---|---|
| Hib-CRM197 conjugate (μg saccharide per dose) | 1.25 | 2.5 | 5 | 10 |
| Diphtheria toxoid (Lf per dose) | | | | 15 |
| Tetanus toxoid (Lf per dose) | | | | 3.2 |
| Inactivated *B. pertussis* organisms (OU per dose) | | | | 15 |
| Aluminium phosphate adjuvant (mg Al$^{3+}$ per dose) | | | | 0.3 |
| NaCl (mg per dose) | | | | 4.5 |
| Merthiolate | | | | Trace |
| Hib fraction relative to ref. 175 | 1/8 | 1/4 | 1/2 | 1 |

The production process was essentially as follows: start with wfi; add the aluminium phosphate adjuvant; add the D component; add the T component; add the wP component; add NaCl; check and adjust pH; and add the Hib component. Contrary to the statement in reference 175, the Hib component does not adsorb to the adjuvant.

Stability

Two stability studies were performed: one under normal storage conditions at 2-8° C. for 2 years, and another under accelerated conditions at 37° C. for 14 days. Vaccines were tested after storage in an upright or an inverted position. Stability was assessed by determining pH and free saccharide.

Results of the first study were as follows:

| | | RELATIVE HIB DOSE | | | |
|---|---|---|---|---|---|
| Months | Parameter | 1 | 1/2 | 1/4 | 1/8 |
| 0 | pH | 6.7 | 6.5 | 6.5 | 6.6 |
| | % free sacc | 2.9 | <3.6 | <7.2 | <14.4 |
| 6 | pH | 6.8 | 6.7 | 6.7 | 6.7 |
| | % free sacc | 2.6 | <3.6 | <7.2 | <14.5 |
| 12 | pH | 7.0 | 6.9 | 6.9 | 7.0 |
| | % free sacc | 4.8 | 5.1 | 2.5 | 4.4 |
| 24 | pH | 7.1 | 7.0 | 7.0 | 7.1 |
| | % free sacc | 6.1 | 5.8 | 5.6 | 5.0 |

Results of the accelerated stability study were as follows:

| | | RELATIVE HIB DOSE | | | |
|---|---|---|---|---|---|
| Time | Parameter | 1 | 1/2 | 1/4 | 1/8 |
| 0 | pH | 6.7 | 6.5 | 6.5 | 6.6 |
| | % free sacc | 2.2 | <3.6 | <7.2 | <14.4 |
| 14 days upright | pH | — | — | — | — |
| | % free sacc | 4.2 | 5.1 | <7.2 | <14.5 |
| 14 days inverted | pH | 6.8 | 6.7 | 6.7 | 6.8 |
| | % free sacc | 5.0 | 5.6 | <7.2 | <14.5 |

The vaccines are thus stable over extended periods. Adsorption was tested over the same timescale, and the Hib conjugate remains unadsorbed during storage.

Clinical Testing

A total of 261 infants were enrolled and randomised to receive one of the four vaccines in a double-blind trial to evaluate safety and immunogenicity (cf. the studies in references 6, 8 and 9, which were either partially blinded or open). Three month-old infants in good health, born at ≥37 weeks of gestation with a minimum birth weight of 2500 g, and eligible for the local EPI, were enrolled and randomised in a 66:65: 65:65 A:B:C:D ratio to receive three single intramuscular doses of one of the vaccines at 3, 4 and 5 months of age. In accordance with the local EPI, subjects received oral polio vaccine (OPV) in parallel at 2, 4 and 6.

Mean age at enrolment was 94 (range 69-108) days and no difference was observed among the four vaccine groups in terms of sex, race, weight and height distribution. Patients were followed for post-injection reactions and adverse events. months of age. A total of 260 subjects were included in the safety analyses (65 for each of the four vaccine groups), and 251 in the immunogenicity analyses (61 in group A, 64 each in groups B and C, and 62 in group D). Nine subjects did not complete the study as their parents/legal guardians withdrew their consent before study completion (5 subjects in group A, 1 subject in group B and 3 subjects in group D).

Blood samples were obtained at baseline and one month after the third dose. Anti-PRP, anti-pertussis, anti-diphtheria and anti-tetanus antibodies were measured. IgG anti-PRP antibodies were measured by a modified ELISA adapted from the FDA ELISA method [176]. IgG anti-diphtheria toxin antibodies and IgG anti-tetanus toxin antibody were quantified by ELISA. Serological markers for *B. pertussis* (anti-pertactin and anti-Agg2-3) were also measured by ELISA.

Safety and Reactogenicity

Subjects were monitored by study staff for 30 minutes after each vaccine dose. Parents were asked to record on a diary the daily rectal temperature and local and systemic reactions for seven days following each injection. Additionally, study personnel actively contacted the parents/legal guardians by telephone on the second and seventh day following each vaccination to obtain particulars of any adverse events. Occurrence of adverse events, or serious adverse events and those necessitating physician visit and/or any medication were critically examined and recorded throughout the study duration. Subjects who received at least one vaccination were included in safety analyses.

Local and systemic reactions were mostly mild and transient. The most frequent were tenderness, erythema and induration for local reactions, and irritability, sleepiness and unusual crying for systemic reactions:

|  | A: 1.25 µg | B: 2.5 µg | C: 5 µg | D: 10 µg |
|---|---|---|---|---|
| Local |  |  |  |  |
| Tenderness - any | 48 (74%) | 53 (82%) | 52 (80%) | 49 (75%) |
| (Cried when injected limb was moved) | 16 (25%) | 19 (29%) | 16 (25%) | 15 (23%) |
| Erythema - any | 31 (48%) | 29 (45%) | 37 (57%) | 31 (48%) |
| (>50 mm) | 6 (9%) | 5 (8%) | 7 (11%) | 4 (6%) |
| Induration - any | 27 (42%) | 21 (32%) | 25 (38%) | 24 (37%) |
| (>50 mm) | 3 (5%) | 4 (6%) | 6 (9%) | 3 (5%) |
| Systemic |  |  |  |  |
| Rash | 3 (5%) | 4 (6%) | 3 (5%) | 3 (5%) |
| Change in Eating Habits | 20 (31%) | 16 (25%) | 26 (40%) | 27 (42%) |
| Sleepiness | 41 (63%) | 49 (75%) | 44 (68%) | 39 (60%) |
| Unusual Crying | 29 (45%) | 23 (35%) | 32 (49%) | 29 (45%) |
| Persistent Crying | 10 (15%) | 8 (12%) | 10 (15%) | 7 (11%) |
| Irritability | 47 (72%) | 53 (82%) | 50 (77%) | 49 (75%) |
| Vomiting | 5 (8%) | 6 (9%) | 9 (14%) | 7 (11%) |
| Diarrhoea | 17 (26%) | 24 (37%) | 22 (34%) | 18 (28%) |
| Other Rectal Temperature |  |  |  |  |
| ≥38.5° C.-<40.5° C. | 14 (22%) | 21 (32%) | 10 (15%) | 12 (18%) |
| ≥40.5° C. | 0 (0%) | 0 (0%) | 0 (0%) | 0 (0%) |
| Use of analgesic/antipyretic medication | 33 (51%) | 43 (66%) | 28 (43%) | 33 (51%) |

No significant differences were observed among the four vaccine groups, and all post-vaccination reactions resolved without sequalae. There were no serious adverse events reported as related to study vaccines.

Immunogenicity

Anti-PRP seroconversion rates (% patients seroconverted) were as follows:

Anti-pertussis seroconversion rates were assessed by looking at (a) increases of anti-pertactin and anti-Agg2-3 responses, and (b) GMTs. Results (% patients) were as follows:

|  | 1.25 µg | 2.5 µg | 5 µg | 10 µg |
|---|---|---|---|---|
| Anti-pertactin |  |  |  |  |
| % patients with 2-fold increase | 91% | 95% | 88% | 94% |
| % patients with 4-fold increase | 80% | 83% | 78% | 89% |
| Anti-pertactin GMT (µg/ml) | 19 | 21 | 24 | 20 |
| Anti-Agg2-3 |  |  |  |  |
| % patients with 2-fold increase | 81% | 81% | 83% | 80% |
| % patients with 4-fold increase | 70% | 80% | 78% | 71% |
| Anti-Agg2-3 GMT (µg/ml) | 87 | 77 | 66 | 76 |

Anti-diphtheria and anti-tetanus GMTs were as follows:

|  | 1.25 µg | 2.5 µg | 5 µg | 10 µg |
|---|---|---|---|---|
| Anti-diphtheria GMT (µg/ml) | 1.33 | 1.65 | 1.49 | 4.70 |
| Anti-tetanus GMT (µg/ml) | 4.89 | 5.10 | 5.24 | 5.16 |

Figure 1:
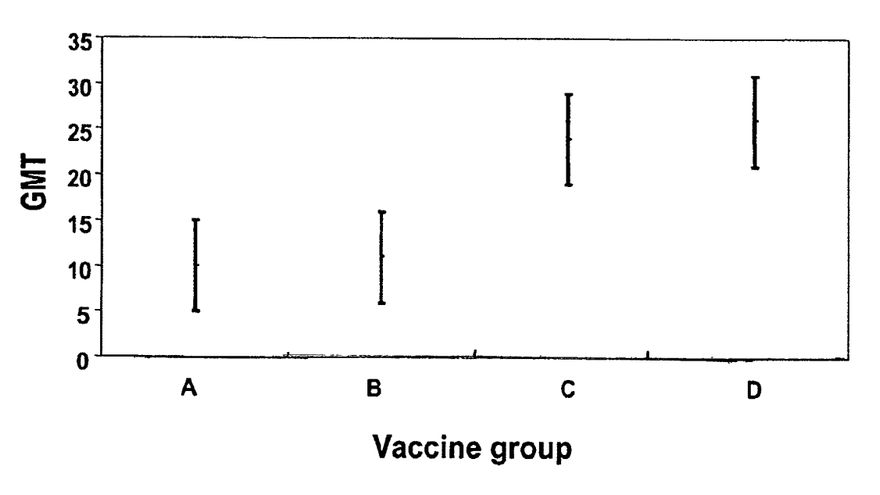
FIG. 1 shows anti-PRP GMTs and 95% confidence intervals in the vaccine groups A, B, C and D.

The proportion of subjects with anti-PRP titres≥0.15 µg/mL was thus similar in the four vaccine groups, but the proportion of subjects with anti-PRP titres≥1.0 µg/mL was higher in groups C and D (97% and 95% respectively) than in groups A and B (90% and 88% respectively). Anti-PRP GMTs show a clear dose-response effect, being similar between groups A (6.94 µg/ml) and B (7.82 µg/ml), and between groups C (17 µg/mL) and D (18 µg/mL), but significantly lower in groups A and B when compared with both C and D groups (FIG. 1).

One month after the third vaccination, all subjects in each of the four vaccine groups seroconverted to diphtheria and tetanus (antibody level≥0.1 IU/mL). No appreciable differences were observed in GMTs among the four vaccine groups.

No differences were observed among the four vaccine groups in the proportion of subjects with a 2- or 4-fold increase of anti-pertactin and anti-Agg2-3 antibodies compared with baseline. GMTs among the four vaccination groups were also similar.

Conclusions

The DTwPHib vaccine formulations with fractional doses of 5, 2.5 or 1.25 µg Hib-conjugate per dose were as immunogenic as the reference 10 µg formulation, as far as seroconversion rates were concerned. High and equivalent levels of anti-PRP GMTs were elicited by the formulations with 10 µg or 5 µg of conjugate. Although formulations with 2.5 µg and 1.25 µg of conjugate per dose elicited lower anti-PRP GMTs, they were adequately immunogenic.

Thus the work confirms that the amount of Hib antigen can be reduced as low as 1.25 µg per dose in an appropriate formulation containing DTP vaccines without affecting the protective efficacy of other vaccine components.

|  | 1.25 µg | | 2.5 µg | | 5 µg | | 10 µg | |
|---|---|---|---|---|---|---|---|---|
| Titre | ≥0.15 µg/ml | ≥1.0 µg/ml | ≥0.15 µg/ml | ≥1.0 µg/ml | ≥0.15 µg/ml | ≥1.0 µg/ml | ≥0.15 µg/ml | ≥1.0 µg/ml |
| Pre | 47% | 12% | 30% | 6% | 32% | 6% | 34% | 4% |
| Post | 98% | 90% | 97% | 88% | 98% | 97% | 100% | 95% |

All four formulations of the DTP-Hib vaccine were safe and immunogenic for all vaccine components. In terms of anti-PRP seroprotection rates, the four formulations were equally immunogenic, both in the short term (titres≥0.15 µg/mL) and in the long term (titres≥1 µg/mL). The formulation containing 5 µg conjugate was as immunogenic as the reference formulation containing 10 µg, and for both formulations the anti-PRP GMTs were particularly high (17 and 18 µg/mL). The formulations containing 1.25 and 2.5 µg conjugate were highly immunogenic when compared with the immune responses observed in other studies using fractional doses of Hib vaccines [6, 8, 9].

Further information can be found in reference 177.

It will be understood that the invention has been described by way of example only and modifications may be made whilst remaining within the scope and spirit of the invention.

REFERENCES

The Contents of which are Hereby Incorporated in Full

[1] Eskola et al. (1996) *Lancet* 348:1688-1692.
[2] Vidor et al. (1999) Chapter 1 of *Combination Vaccines* (ed. Ellis) ISBN 0-89603-717-7.
[3] Corbel (1996) *Dev Biol Stand* 87:113-124.
[4] Campbell et al. (2002) *Pediatr Infect Dis J* 21:822-826.
[5] Guimaraes et al. (2002) *Int J Infect Dis* 6:113-117.
[6] Lagos et al. (1998) *Lancet* 351:1472-1476.
[7] Amir et al. (1997) *Vaccine* 15:149-154.
[8] Fernandez et al. (2000) *Am J Trop Med Hyg* 62:485-490.
[9] Nicol et al. (2002) *Pediatr Infect Dis J* 21:138-141.
[10] WO02/00249.
[11] *Vaccines* (ed. Plotkin et al.) Fourth Edition, ISBN 0-7216-9688-0.
[12] Gustafsson et al. (1996) *N. Engl. J. Med.* 334:349-355.
[13] Rappuoli et al. (1991) *TIBTECH* 9:232-238.
[14] Rappuoli (1997) *Nature Medicine* 3:374-376.
[15] Ramsay et al. (2001) *Lancet* 357(9251):195-196.
[16] Lindberg (1999) *Vaccine* 17 Suppl 2:S28-36.
[17] Buttery & Moxon (2000) *J R Coll Physicians Lond* 34:163-168.
[18] Ahmad & Chapnick (1999) *Infect Dis Clin North Am* 13:113-133, vii.
[19] Goldblatt (1998) *J. Med. Microbiol.* 47:563-567.
[20] European patent 0477508.
[21] U.S. Pat. No. 5,306,492.
[22] WO98/42721.
[23] *Conjugate Vaccines* (eds. Cruse et al.) ISBN 3805549326, particularly vol. 10:48-114.
[24] Hermanson (1996) *Bioconjugate Techniques* ISBN: 0123423368 or 012342335X.
[25] Anonymous (January 2002) *Research Disclosure*, 453077.
[26] Anderson (1983) *Infect Immun* 39(1):233-238.
[27] Anderson et al. (1985) *J Clin Invest* 76(1):52-59.
[28] EP-A-0372501.
[29] EP-A-0378881.
[30] EP-A-0427347.
[31] WO93/17712
[32] WO94/03208.
[33] WO98/58668.
[34] EP-A-0471177.
[35] WO91/01146
[36] Falugi et al. (2001) *Eur J Immunol* 31:3816-3824.
[37] EP-A-0594610.
[38] WO00/56360.
[39] WO02/091998.
[40] WO01/72337
[41] WO00/61761.
[42] WO96/40242
[43] Lees et al. (1996) *Vaccine* 14:190-198.
[44] WO95/08348.
[45] U.S. Pat. No. 4,882,317
[46] U.S. Pat. No. 4,695,624
[47] Porro et al. (1985) *Mol Immunol* 22:907-919.
[48] EP-A-0208375
[49] WO00/10599
[50] Gever et al. *Med. Microbiol. Immunol*, 165: 171-288 (1979).
[51] U.S. Pat. No. 4,057,685.
[52] U.S. Pat. Nos. 4,673,574; 4,761,283; 4,808,700.
[53] U.S. Pat. No. 4,459,286.
[54] U.S. Pat. No. 4,965,338.
[55] U.S. Pat. No. 4,663,160.
[56] U.S. Pat. No. 4,761,283
[57] U.S. Pat. No. 4,356,170
[58] Lei et al. (2000) *Dev Biol (Basel)* 103:259-264.
[59] WO00/38711; U.S. Pat. No. 6,146,902.
[60] Kanra et al. (1999) *The Turkish Journal of Paediatrics* 42:421-427.
[61] Ravenscroft et al. (2000) *Dev Biol (Basel)* 103: 35-47.
[62] Sturgess et al. (1999) *Vaccine* 17:1169-1178.
[63] WO97/00697.
[64] WO96/37222; U.S. Pat. No. 6,333,036.
[65] *Vaccine Design* . . . (1995) eds. Powell & Newman. ISBN: 030644867X. Plenum.
[66] WO00/23105.
[67] WO90/14837.
[68] U.S. Pat. No. 5,057,540.
[69] WO96/33739.
[70] EP-A-0109942.
[71] WO96/11711.
[72] WO00/07621.
[73] Barr et al. (1998) *Advanced Drug Delivery Reviews* 32:247-271.
[74] Sjolanderet et al. (1998) *Advanced Drug Delivery Reviews* 32:321-338.
[75] Niikura et al. (2002) *Virology* 293:273-280.
[76] Lenz et al. (2001) *J Immunol* 166:5346-5355.
[77] Pinto et al. (2003) *J Infect Dis* 188:327-338.
[78] Gerber et al. (2001) *Virol* 75:4752-4760.
[79] WO03/024480
[80] WO03/024481
[81] Gluck et al. (2002) *Vaccine* 20:B10-B16.
[82] EP-A-0689454.
[83] Johnson et al. (1999) *Bioorg Med Chem Lett* 9:2273-2278.
[84] Evans et al. (2003) *Expert Rev Vaccines* 2:219-229.
[85] Meraldi et al. (2003) *Vaccine* 21:2485-2491.
[86] Pajak et al. (2003) *Vaccine* 21:836-842.
[87] Kandimalla et al. (2003) *Nucleic Acids Research* 31:2393-2400.
[88] WO02/26757.
[89] WO99/62923.
[90] Krieg (2003) *Nature Medicine* 9:831-835.
[91] McCluskie et al. (2002) *FEMS Immunology and Medical Microbiology* 32:179-185.
[92] WO98/40100.
[93] U.S. Pat. No. 6,207,646.
[94] U.S. Pat. No. 6,239,116.
[95] U.S. Pat. No. 6,429,199.
[96] Kandimalla et al. (2003) *Biochemical Society Transactions* 31 (part 3):654-658.

[97] Blackwell et al. (2003) *J Immunol* 170:4061-4068.
[98] Krieg (2002) *Trends Immunol* 23:64-65.
[99] WO01/95935.
[100] Kandimalla et al. (2003) *BBRC* 306:948-953.
[101] Bhagat et al. (2003) *BBRC* 300:853-861.
[102] WO03/035836.
[103] WO95/17211.
[104] WO98/42375.
[105] Beignon et al. (2002) *Infect Immun* 70:3012-3019.
[106] Pizza et al. (2001) *Vaccine* 19:2534-2541.
[107] Pizza et al. (2000) *Int J Med Microbiol* 290:455-461.
[108] Scharton-Kersten et al. (2000) *Infect Immun* 68:5306-5313.
[109] Ryan et al. (1999) *Infect Immun* 67:6270-6280.
[110] Partidos et al. (1999) *Immunol Lett* 67:209-216.
[111] Peppoloni et al. (2003) *Expert Rev Vaccines* 2:285-293.
[112] Pine et al. (2002) *J Control Release* 85:263-270.
[113] Domenighini et al. (1995) *Mol Microbiol* 15:1165-1167.
[114] WO99/40936.
[115] WO99/44636.
[116] Singh et all (2001) *J Cont Release* 70:267-276.
[117] WO99/27960.
[118] U.S. Pat. No. 6,090,406
[119] U.S. Pat. No. 5,916,588
[120] EP-A-0626169.
[121] WO99/52549.
[122] WO01/21207.
[123] WO01/21152.
[124] Andrianov et al. (1998) *Biomaterials* 19:109-115.
[125] Payne et al. (1998) *Adv Drug Delivery Review* 31:185-196.
[126] Stanley (2002) *Clin Exp Dermatol* 27:571-577.
[127] Jones (2003) *Curr Opin Investig Drugs* 4:214-218.
[128] WO99/11241.
[129] WO94/00153.
[130] WO98/57659.
[131] European patent applications 0835318, 0735898 and 0761231.
[132] Costantino et al. (1992) *Vaccine* 10:691-698.
[133] WO03/007985.
[134] Watson (2000) *Pediatr Infect Dis J* 19:331-332.
[135] Rubin (2000) *Pediatr Clin North Am* 47:269-285, v.
[136] Jedrzejas (2001) *Microbiol Mol Biol Rev* 65:187-207.
[137] Bell (2000) *Pediatr Infect Dis J* 19:1187-1188.
[138] Iwarson (1995) *APMIS* 103:321-326.
[139] Gerlich et al. (1990) *Vaccine* 8 Suppl:S63-68 & 79-80.
[140] Bjune et al. (1991) *Lancet* 338(8775):1093-96
[141] WO01/52885.
[142] Fukasawa et al. (1999) *Vaccine* 17:2951-2958.
[143] Rosenqvist et al. (1998) *Dev. Biol. Stand.* 92:323-333.
[144] WO99/24578.
[145] WO99/36544.
[146] WO99/57280.
[147] WO00/22430.
[148] Tettelin et al. (2000) *Science* 287:1809-1815.
[149] WO96/29412.
[150] Pizza et al. (2000) *Science* 287:1816-1820.
[151] Sutter et al. (2000) *Pediatr Clin North Am* 47:287-308.
[152] Zimmerman & Spann (1999) *Am Fam Physician* 59:113-118, 125-126.
[153] Robinson & Tones (1997) *Seminars in Immunology* 9:271-283.
[154] Donnelly et al. (1997) *Annu Rev Immunol* 15:617-648.
[155] Scott-Taylor & Dalgleish (2000) *Expert Opin Investig Drugs* 9:471-480.
[156] Apostolopoulos & Plebanski (2000) *Curr Opin Mol Ther* 2:441-447.
[157] Ilan (1999) *Curr Opin Mol Ther* 1:116-120.
[158] Dubensky et al. (2000) *Mol Med* 6:723-732.
[159] Robinson & Pertmer (2000) *Adv Virus Res* 55:1-74.
[160] Donnelly et al. (2000) *Am J Respir Crit Care Med* 162(4 Pt 2):S190-193.
[161] Davis (1999) *Mt. Sinai J. Med.* 66:84-90.
[162] Charalambous & Feavers (2001) *J Med Microbiol* 50:937-939.
[163] Westerink (2001) *Int Rev Immunol* 20:251-261.
[164] Grothaus et al. (2000) *Vaccine* 18:1253-1263.
[165] Paoletti et al. (2001) *Vaccine* 19:2118-2126.
[166] WO00/56365.
[167] Gennaro (2000) *Remington: The Science and Practice of Pharmacy*. 20th edition, ISBN: 0683306472.
[168] WO03/009869.
[169] WO01/30390.
[170] Almeida & Alpar (1996) *J. Drug Targeting* 3:455-467.
[171] Agarwal & Mishra (1999) *Indian J Exp Biol* 37:6-16.
[172] Bergquist et al. (1998) *APMIS* 106:800-806.
[173] Ryan et al. (1999) *Infect Immun* 67(12):6270-6280.
[174] Nagai et al. (2001) *Vaccine* 19:4824-4834.
[175] Botet Asensi et al. (2003) *Acta Paediatrica* 92:541-545.
[176] Mariani et al. (1988) *Clin Diagn Lab Immunol* 5:667-674.
[177] Tamm et al. (2005) *Vaccine* 23:1715-1719.

The invention claimed is:

1. A liquid combination vaccine comprising antigens for protecting a subject against at least diphtheria ('D'), tetanus ('T'), pertussis ('P') and *Haemophilus influenzae* type b ('Hib'), wherein: (a) the antigen for protecting against Hib is a conjugate of a Hib capsular saccharide; (b) the concentration of the Hib conjugate in the vaccine is <15 µg/ml; (c) the vaccine comprises an aluminium phosphate adjuvant; (d) no more than 15% by weight of the Hib conjugate in the vaccine is adsorbed to aluminium phosphate; (e) the vaccine does not contain an aluminium hydroxide adjuvant; (f) the vaccine does not contain an aluminium potassium sulphate adjuvant; and (g) the vaccine contains an $Al^{3+}$ concentration of 0.1-1.0 mg/ml.

2. A vial having a piercable seal and containing a liquid combination vaccine, which combination vaccine comprises antigens for protecting a subject against at least diphtheria, tetanus, pertussis and *H. influenzae* type b ('Hib'), wherein the antigen for protecting against Hib is a conjugate of a Hib capsular saccharide, and wherein: (a) the concentration of the Hib conjugate in the vaccine is <15 µg/ml, (b) the vial's piercable seal has not been pierced; (c) the vaccine comprises an aluminium phosphate adjuvant; (d) no more than 15% by weight of the Hib conjugate in the vaccine is adsorbed to aluminium phosphate; (e) the vaccine does not contain an aluminium hydroxide adjuvant; (f) the vaccine does not contain an aluminium potassium sulphate adjuvant; and (g) the vaccine contains an $Al^{3+}$ concentration of 0.1-1.0 mg/ml.

3. A hermetically-sealed container containing a liquid combination vaccine comprising antigens for protecting a subject against at least diphtheria, tetanus, pertussis and *H. influenzae* type b ('Hib'), wherein (a) the antigen for protecting against Hib is a conjugate of a Hib capsular saccharide; (b) the concentration of the Hib conjugate in the vaccine is <15 µg/ml; (c) the vaccine comprises an aluminium phosphate adjuvant; (d) no more than 15% by weight of the Hib conjugate in the vaccine is adsorbed to aluminium phosphate; (e) the vaccine does not contain an aluminium hydroxide adjuvant; (f) the vaccine does not contain an aluminium potassium sulphate adjuvant; and (g) the vaccine contains an $Al^{3+}$ concentration of 0.1-1.0 mg/ml.

4. The vaccine of claim 1, wherein the diphtheria antigen comprises a diphtheria toxoid, the tetanus antigen comprises a tetanus toxoid, and the pertussis antigen comprises a cellular pertussis component.

5. The vial of claim 2, wherein the diphtheria antigen comprises a diphtheria toxoid, the tetanus antigen comprises a tetanus toxoid, and the pertussis antigen comprises a cellular pertussis component.

6. The container of claim 3, wherein the diphtheria antigen comprises a diphtheria toxoid, the tetanus antigen comprises a tetanus toxoid, and the pertussis antigen comprises a cellular pertussis component.

7. The vaccine of claim 1, wherein the conjugate comprises a $CRM_{197}$ carrier, a tetanus toxoid carrier or an outer membrane complex of N. meningitidis carrier.

8. The vial of claim 2, wherein the conjugate comprises a $CRM_{197}$ carrier, a tetanus toxoid carrier or an outer membrane complex of N. meningitidis carrier.

9. The container of claim 3, wherein the conjugate comprises a $CRM_{197}$ carrier, a tetanus toxoid carrier or an outer membrane complex of N. meningitidis carrier.

10. The vaccine of claim 1, wherein the conjugate comprises an oligosaccharide fragment of the Hib polyribosylribitol phosphate.

11. The vial of claim 2, wherein the conjugate comprises an oligosaccharide fragment of the Hib polyribosylribitol phosphate.

12. The container of claim 3, wherein the conjugate comprises an oligosaccharide fragment of the Hib polyribosylribitol phosphate.

13. The vaccine of claim 1, wherein at most 5% of the Hib conjugate in the vaccine is adsorbed to aluminium phosphate.

14. The vial of claim 2, wherein at most 5% of the Hib conjugate in the vaccine is adsorbed to aluminium phosphate.

15. The container of claim 3, wherein at most 5% of the Hib conjugate in the vaccine is adsorbed to aluminium phosphate.

16. The vaccine of claim 4, wherein the diphtheria toxoid and the tetanus toxoid are adsorbed onto aluminium phosphate.

17. The vaccine of claim 13, wherein at most 1% of the Hib conjugate in the vaccine is adsorbed to aluminium phosphate.

18. The vaccine of claim 1, wherein the conjugate has a saccharide:protein ratio (w/w) of between 1:5 and 5:1.

19. The vial of claim 2, wherein the conjugate has a saccharide:protein ratio (w/w) of between 1:5 and 5:1.

20. The container of claim 3, wherein the conjugate has a saccharide:protein ratio (w/w) of between 1:5 and 5:1.

21. The liquid combination vaccine of claim 1, wherein the $Al^{3+}$ concentration is 0.1-0.6 mg/ml.

22. The vial of claim 2, wherein the $Al^{3+}$ concentration in (g) is 0.1-0.6 mg/ml.

23. The hermetically-sealed container of claim 3, wherein the $Al^{3+}$ concentration in (g) is 0.1-0.6 mg/ml.

* * * * *